United States Patent [19]

Sherlock

[11] Patent Number: 4,596,809

[45] Date of Patent: Jun. 24, 1986

[54] SUBSTITUTED 1,8-NAPHTHYRIDINONES, USEFUL AS ANTI-ALLERGIC AGENTS

[75] Inventor: Margaret H. Sherlock, Bloomfield, N.J.

[73] Assignee: Schering Corporation, Kenilworth, N.J.

[21] Appl. No.: 716,003

[22] Filed: Mar. 25, 1985

[51] Int. Cl.⁴ .............. A61K 31/435; A61K 31/495; C07D 491/12

[52] U.S. Cl. .................................. 514/293; 546/83; 546/15; 544/345; 544/361; 544/126

[58] Field of Search ................ 546/83, 15; 544/345, 544/361, 126; 514/293

[56] References Cited

FOREIGN PATENT DOCUMENTS 0127135  5/1984  European Pat. Off. .............. 546/83

*Primary Examiner*—Henry R. Jiles
*Assistant Examiner*—J. Richter
*Attorney, Agent, or Firm*—Anita W. Magatti; Stephen T. Miller

[57] ABSTRACT

Substituted 1,8-naphthyridinones are anti-allergic, anti-inflammatory and cytoprotective agents. Methods for their preparation and use are disclosed.

18 Claims, No Drawings

SUBSTITUTED 1,8-NAPHTHYRIDINONES, USEFUL AS ANTI-ALLERGIC AGENTS

BACKGROUND OF THE INVENTION

The present invention relates to novel tricyclc compounds which possess anti-allergic, anti-inflammatory and cytoprotective activity.

SUMMARY OF THE INVENTION

The compounds of this invention are represented by the formulae

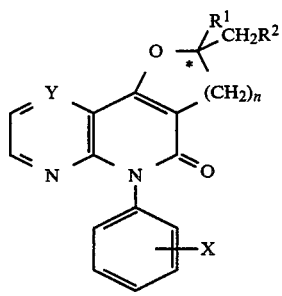
I

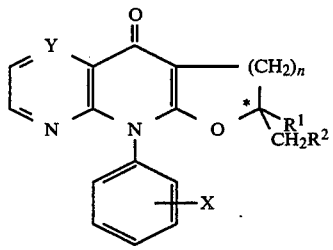
II

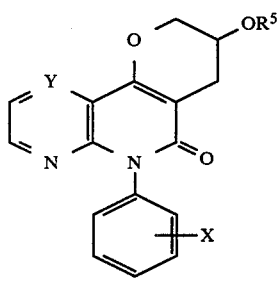
III wherein n is 1 or 2;

$R^1$ and $R^2$ may be combined to form a bond, or $R^1$ is hydrogen and $R^2$ is OR, halogen or $NR^3R^4$;

R is hydrogen, carboxylic acyl having from 2 to 10 carbon atoms, or carbamyl;

$R^3$ and $R^4$ are independently hydrogen or alkyl having from 1 to 6 carbon atoms, or $R^3$ and $R^4$ may be combined with the nitrogen to which they are attached to form a pyrrolidino, piperidino, morpholino, or piperazino ring;

$R^5$ is hydrogen or carboxylic acyl having from 2 to 10 carbon atoms;

X is hydrogen, hydroxy, alkyl having 1 to 6 carbon atoms, alkoxy having from 1 to 6 carbon atoms, nitro, halogen, alkyl-S(O)$_m$ having from 1 to 6 carbon atoms and wherein m is 0, 1 or 2, or trifluoromethyl; and Y is CH or N; and the acid addition salts thereof.

It is contemplated that there may be 1 to 3 "X" substituents on the phenyl ring. As used herein, the term "alkyl" refers to straight or branched chain groups, e.g. methyl, ethyl, propyl, isopropyl, butyl, isobutyl and hexyl. Examples of "alkoxy" groups are methoxy, ethoxy, isopropoxy, butoxy and hexoxy. "Halogen" refers to fluorine, chlorine and bromine.

As used herein, the term "carboxylic acyl" refers to the radical obtained by removing the hydroxyl group from the corresponding carboxylic acid, i.e. radicals of the formula

wherein $R^6$ is for example alkyl of 1 to 9 carbon atoms, phenyl and substituted phenyl wherein the substituents are as defined for X, benzyl, alkenyl of 2 to 7 carbon atoms or alkynyl of 2 to 7 carbon atoms. Similarly, "carbamyl" refers to the radical obtained by removing the hydroxy group from the corresponding carbamic acid, i.e. radicals of the formula

wherein $R^7$ and $R^8$ are independently hydrogen, lower alkyl having from 1 to 6 carbon atoms, and hydroxyalkyl having from 1 to 6 carbon atoms.

The term "acid addition salts" as used herein refers to salts formed with pharmaceutically acceptable acids such as hydrochloric, hydrobromic, methane sulfonic and sulfuric acids.

Preferred are compounds of formulae I or II, with compounds of formula I being more preferred.

Preferred compounds of formulae I and II are those wherein n is 1.

A third group of preferred compounds is that wherein Y is CH.

A fourth group of preferred compounds is that wherein $R^1$ is hydrogen and $R^2$ is OR wherein R is hydrogen or carboxylic acyl.

Still another group of preferred compounds is that wherein X is hydrogen or meta-halogeno. A preferred meta-halogeno group is meta-chloro.

Also contemplated as part of this invention are pharmaceutical compositions which comprise a compound of formulae I, II or III in combination with a pharmaceutically acceptable carrier.

In addition, the invention contemplates two aspects of pharmaceutical methods:

The invention sought to be patented in a first pharmaceutical method aspect is a method for treating allergic reactions in a mammal which comprises administering an anti-allergic effective amount of the above-defined pharmaceutical composition to said mammal.

The invention sought to be patented in a second pharmaceutical method aspect is a method for treating inflammation in a mammal which comprises administering an anti-inflammatory effective amount of the above-defined pharmaceutical composition to said mammal.

It is also contemplated that compounds of the invention are useful in the treatment of peptic ulcers.

DESCRIPTION OF THE INVENTION

The compounds of this invention may be prepared by methods known to those skilled in the art. An example of such a method for preparing compounds of formulae I and III wherein Y is CH is shown in the following reaction scheme:

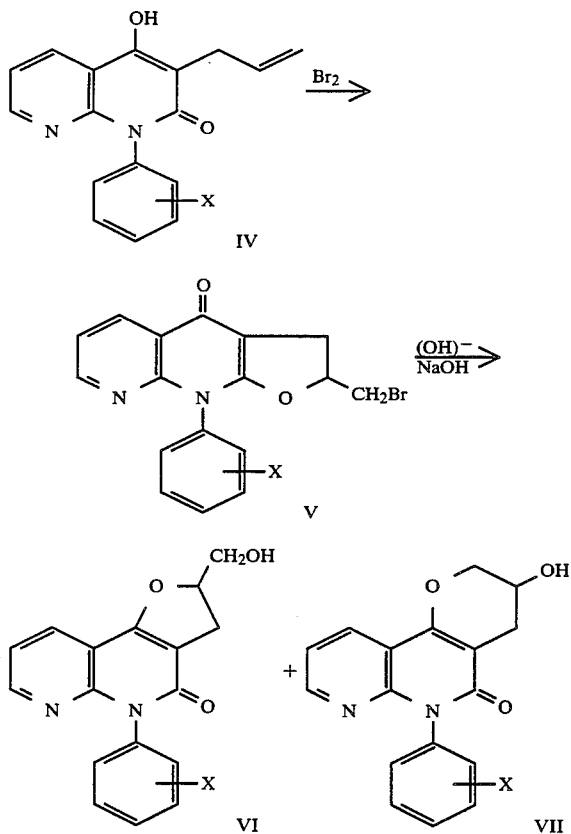

wherein X is as defined above. In the above scheme, bromination of the starting material of formula IV results in the spontaneous cyclization of the intermediate dibromo compound to the compound of formula V. In the presence of aqueous sodium hydroxide, the compound of formula V undergoes hydrolysis to yield compounds of formulae VI and VII.

An example of a method of preparing compounds of formula II wherein Y is CH and $R^2$ is $NR^3R^4$ is described in the following reaction scheme:

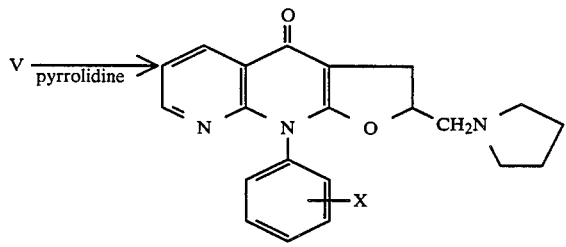

Compounds of formula IV may be prepared by methods known in the art. See, for example, U.S. Pat. No. 4,492,702. An example of such a procedure is provided in Preparation 1.

Compounds of this invention wherein Y is N may be similarly prepared using starting materials analogous to the compounds of formula IV. That is, 2-phenylamino-3-pyrazine carboxylates may be used in place of 2-phenylamino-3-pyridine carboxylates in Part A of Preparation 1 to prepare pyrazino-pyridine compounds in place of naphthyridinones.

For the preparation of compounds of formulae I or II wherein $R^1$ is hydrogen and $R^2$ is OR wherein R is acyl and compounds of formula III wherein $R^5$ is acyl, standard acylation techniques may be used, e.g. refluxing the corresponding alcohol with an acid anhydride in an inert solvent such as benzene.

Compounds of formulae I or II wherein $R^2$ is $NR^3R^4$ may be prepared for example, through the reaction of the corresponding 2-halomethyl compound and the appropriate amine.

Compounds wherein $R^1$ and $R^2$ form a bond may also be prepared by standard techniques, e.g. by dehydrohalogenation of the halomethyl side chain in the presence of a base.

Compounds of formulae I and II wherein $R^1$ is hydrogen have at least one asymmetric carbon atom, i.e., the carbon indicated with an asterisk(*) in formulae I and II. The compounds accordingly exist in enantiomeric forms or in racemic mixtures thereof, and all such isomers and racemic mixtures are within the scope of this invention. Separation of the isomers may be accomplished by methods well known to those skilled in the art.

The compounds of this invention can be used to treat allergy cused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylactic bronchospasm in sensitized rats having antigen induced bronchoconstriction. For example, the compound 3,5-dihydro-2-(hydroxymethyl)-5-phenyl-furo-[3,2-c]-1,8-naphthyridin-4(2H)-one was found to inhibit anaphylactic bronchospasm in such a test procedure when given at an oral dose of 2 mg/kg. Said compound was also found to inhibit allergen-induced histamine release from guinea pig sensitized tissue. The compounds are effective non-adrenergic, non-anticholinergic antianaphylactic agents. When administered orally they are active at doses from about 0.1 to 10 mg/kg of body weight; when administered parenterally, e.g., intravenously, the compounds are active at dosages of from about 0.05 to 5 mg/kg body weight; when administered by inhalation (aerosol or nebulizer) the compounds are active at dosages of about 0.25 to 5 mg per puff, and one to four puffs may be taken every 4 hours.

The compounds of this invention are also useful for the treatment of inflammation. The anti-inflammatory use of the compounds of the present invention may be demonstrated by the Reversed Passive Arthus Reaction (RPAR) Rat Paw technique as set forth below. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

RPAR Rat Paw Technique

Animals, Materials and Methods

Male Lewis inbred albino rats weighing 180-200 grams obtained from Charles River Breeding Laboratories are used in these experiments. The rats are housed 3 animals/cage and food and water are allowed ad libitum. The animals are numbered 1-3 in each cage and color marked for identification purposes.

Drug and Reagent Preparation

All reagents and drugs are prepared just prior to the study. Crystallized and lyophilized bovine serum albumin (BSA), obtained from Sigma Chemical Company, is solubilized without shaking in cold sterile pyrogen free saline (10 mg/ml). Lyophilized anti-bovine serum albumin (IGG fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Drug Administration and Induction of Inflammation

Groups of animals (6/group) are dosed with drug in MC by gavage once daily for 3 days. The last dose is administered one hour prior to sensitization with BSA. Controls are given MC alone and a drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after the last dose the animals are lightly anesthetized with ether and "sensitized" by injection into the penile vein with 0.2 ml of PFS containing 1.0 mg of BSA. One hour later, the animals are "challenged" in the right rear paw with subplantar injections of 0.2 ml of PFS containing 0.1 mg of anti-BSA. Immediately after the subplantar injection, the right paw is dipped (up to the lateral maleolus) into the mercury well of a plethysmograph. The volume of mercury displaced is converted to weight and recorded. This value is considered to be the control reading for the animal. Paw volumes are also recorded with a plethysmograph during the development of the inflammation at 2 and 4 hours post-challenge.

Results

Results are expressed by the change in paw volume (Δ paw volume) from the control reading for each animal to that recorded 2 and 4 hours post-challenge. All drug treated groups are compared to the MC control for significant differences with an analysis of variance. Differences from control in drug-treated groups are expressed as percent change from control.

When administered parenterally, e.g. intravenously, the compounds are administered at a dosage range of about 0.01-10 mg/kg of body weight in single or multiple daily doses.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like.

The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

PREPARATION AND EXAMPLES

PREPARATION 1

4-HYDROXY-1-PHENYL-3-(2-PROPENYL)-1,8-NAPHTHYRIDIN-2(1H)-ONE (A) 4-Hydroxy-1-phenyl-1,8-naphthyridin-2(1H)-one To a stirred solution of 1 kg. of methyl 2-phenylamino-3-pyridine carboxylate in 3.97 liters of n-butyl acetate there is added portionwise, 1.1 kg. of potassium tertiary butoxide. After the addition of the potassium tertiary butoxide, there is added an additional 1.32 liters of n-butyl acetate. The reaction mixture is heated to reflux for 20 hours during which the internal temperature of the reaction mixture rises from 90° C. to 122° C. During this period, 1.8 liters of liquid is removed from the reaction via a Dean-Stark trap. Xylene (3.0 liters) is added to the reaction mixture and the remainder of the n-butyl acetate is removed via the Dean-Stark trap. The reaction mixture is cooled and the potassium salt is collected by filtration, washed with toluene and air dried. The crude potassium salt is dissolved in 12 liters of water, the aqueous solution is extracted with toluene, acidified to pH 2 and the product filtered and dried; weight 937 g., m.p. 311°–313° C.

(B) 4-Acetyloxy-1-phenyl-3-(2-propenyl)-1,8-naphthyridin-2(1H)-one (1.) 1-phenyl-4-(2-propenyloxy)-1,8-naphthyridin-2(1H)-one:

To a mixture of 62 g. of 4-hydroxy-1-phenyl-1,8-naphthyridin-2(1H)-one, 39.6 g. of anhydrous potassium carbonate and 1,800 ml of acetone, there is added dropwise, with stirring, 37.5 g. of allyl bromide. The reaction mixture is refluxed for 22 hours, concentrated in vacuo, and the residue extracted with 600 ml. of chloroform. The organic extract is washed with water, 1N sodium hydroxide solution and again with water, dried over anhydrous magnesium sulfate, filtered and concentrated. The crude solid is triturated with 3×400 ml of boiling isopropyl ether and filtered, yielding the insoluble product, wt. 38.5 g., m.p. 171°–174°. Recrystallization from methanol produces the product as a colorless solid, m.p. 176°–177° C.

(2.) 4-Acetyloxy-1-phenyl-3-(2-propenyl)-1,8-naphthyridin-2(1H)-one:

A mixture of 33.8 g. of 1-phenyl-4-(2-propenyloxy)-1,8-naphthyridin-2(1H)-one and 35 ml. of acetic anhydride is refluxed for four hours. On cooling, the reaction mixture solidified. Trituration with isopropyl ether and filtration yields the product, 36.1 g., as a colorless solid, m.p. 189°–195° C. Recrystallization from ethanol provides the product with m.p. 195°–196° C.

(C) 4-Hydroxy-1-phenyl-3-(2-propenyl)-1,8-naphthyridin-2(1H)-one

A mixture of 6.0 g. of 4-acetyloxy-1-phenyl-3-(2-propenyl)-1,8-naphthyridin-2(1H)-one, 200 ml. of ethanol and 40 ml. of 1N sodium hydroxide solution is stirred at room temperature for 22 hours. The ethanol is removed in vacuo and the remaining aqueous solution acidified with 1N hydrochloric acid. The product is filtered, washed with water and dried, weight 5.3 g., m.p. 248°–250° C. Recrystallization from chloroform yields the product of this preparation as a colorless solid, m.p. 250°–252° C.

In a similar manner, substitute 4-bromo-1-butene for allyl bromide in part B(1) of Preparation 1 to prepare 3-(3-butenyl)-4-hydroxy-1-phenyl-1,8-naphthyridin-2(1H)-one.

EXAMPLE 1

2-(BROMOMETHYL)-3,9-DIHYDRO-9-PHENYL-FURO(2,3-b)-1,8-NAPHTHYRIDIN-4(2H)-ONE

To a cooled (5°) solution of 24.5 g. (0.076 moles) of 4-(acetyloxy)-1-phenyl-3-(2-propenyl)-1,8-naphthyridin-2(1H)-one in 350 ml. of dry chloroform there is added dropwise, 12.2 g. (0.076 moles) of bromine. The reaction mixture is allowed to come to room temperature, stirred for 18 hours, concentrated in vacuo, and the solid product is triturated with 3×150 ml. of isopropyl ether and filtered. The crude hydrobromide salt melts at 209°–211° (dec), and on recrystallization from ethanol melts at 212°–213° (dec).

The hydrobromide salt is readily treated with cold 0.1N sodium hydroxide solution, then recrystallized from ethyl acetate to yield the title compound, m.p. 187°–188° C.

EXAMPLE 2

3,5-DIHYDRO-2-(HYDROXYMETHYL)-5-PHENYL-FURO(3,2-c)-1,8-NAPHTHYRIDIN-4(2H)-ONE

A solution of 15.0 g. of 2-(bromomethyl)-3,9-dihydro-9-phenyl-furo(2,3-b)-1,8-naphthyridin-4(2H)-one hydrobromide in 200 ml of methanol, 160 ml of 1.0N sodium hydroxide solution and 150 ml. of water is stirred and refluxed on a steam bath for 21 hours. The reaction is concentrated to a volume of 200 ml in vacuo and the solid filtered and washed with water. Recrystallization of the crude solid from methanol yields the title compound, m.p. 267°–268°.

EXAMPLE 3

2-(ACETYLOXYMETHYL)-3,5-DIHYDRO-5-PHENYL-FURO(3,2-c)-1,8-NAPHTHYRIDIN-4(2H)-ONE

The product of Example 2 is refluxed with acetic anhydride in benzene, and the resultant product is recrystallized from isopropyl acetate to give the title compound, m.p. 207°–208° C.

EXAMPLE 4

3-ACETYLOXY-2,3,4,6-TETRAHYDRO-6-PHENYL-5H-PYRANO(3,2-c)-1,8-NAPHTHYRIDIN-5-ONE

A solution of 51.0 g. of 2-(bromomethyl)-3,9-dihydro-9-phenyl-furo(2,3-b)-1,8-naphthyridin-4(2H)-one, 680 ml. of methanol, 545 ml. of 1.0N sodium hydroxide solution and 510 ml. of water is stirred and refluxed on a steam bath for 18 hours. The solution is concentrated in vacuo to a volume of 600 ml., cooled, and the solids filtered and washed with water. Spectral data and chromatography indicated the presence of two compounds, the product of Example 2 and the title compound of this example.

The crude mixture is acetylated with acetic anhydride in refluxing benzene, yielding a mixture of the acetates. The compounds are separated by chromatography on a Type 60G silica gel column with an ethyl acetate:chloroform(1:1) solution. Recrystallize the furo(2,3-b)isomer from ethyl acetate; filter and recover from the filtrate the title compound, m.p. 224°–226° C.

EXAMPLE 5

3-HYDROXY-2,3,4,6-TETRAHYDRO-6-PHENYL-5H-PYRANO(3,2-c)-1,8-NAPHTHYRIDIN-5-ONE

Hydrolysis of the product of Example 4 with methanol:1.0N sodium hydroxide solution followed by recrystallization of the resultant product from methanol yields the title compound, m.p. 296°–298° C.

EXAMPLE 6

2-(BROMOMETHYL)-3,9-DIHYDRO-9-(3-METHOXYPHENYL)-FURO(2,3-b)-1,8-NAPHTHYRIDIN-4(2H)-ONE

Treat 4-hydroxy-1-(3-methoxyphenyl)-3-(2-propenyl)-1,8-naphthyridin-2(1H)-one according to the procedure described in Example 1, recrystallizing from methanol:ethyl acetate to obtain the title compound, m.p. 196°–198° C.

EXAMPLE 7

2-(ACETYLOXYMETHYL)-3,5-DIHYDRO-5-(3-METHOXYPHENYL)-FURO-(3,2-c)-1,8-NAPHTHYRIDIN-4(2H)-ONE

Treat 2-(bromomethyl)-3,9-dihydro-9-(3-methoxyphenyl)-furo(2,3-b)-1,8-naphthyridin-4(2H)-one according to the procedure of Example 2 to prepare the 2-hydroxymethyl analog of the title compound. Treat this 2-hydroxymethyl compound according to the procedures of Example 3 to obtain the title compound, m.p. 183°–184° C.

EXAMPLE 8

3,9-DIHYDRO-2-(IODOMETHYL)-9-PHENYL-FURO(2,3-b)-1,8-NAPHTHYRIDIN-4(2H)-ONE

To a solution of 4.0 g. (0.014 moles) of 4-hydroxy-1-phenyl-3-(2-propenyl)-1,8-naphthyridin-2(1H)-one in 380 ml. of tetrahydrofuran, there is added, dropwise, with stirring at 3°–5° C., 4.0 g. of 70% perchloric acid in 11.5 ml. of water, followed by the slow addition of 10.2 g. of N-iodo-succinimide over a period of 45 minutes. The reaction is stirred at room temperature for three hours, treated with a saturated solution of sodium sulfite, and extracted with 2×250 ml. of ether. The organic layer is dried over magnesium sulfate, filtered and concentrated to a solid residue. The crude products are separated on a 60G silica gel column with methanol:chloroform (5:95). The desired fraction is recrystallized from ethyl acetate to yield the title compound, m.p. 178°–180° C.

EXAMPLE 9

3,5-DIHYDRO-2(IODOMETHYL)-5-PHENYL-FURO(3,2-c)-1,8-NAPHTHYRIDIN-4(2-H)-ONE

The desired fraction comprising the compound of this example isolated from the column chromatography carried out in Example 8 is recrystallized from acetonitrile to yield the title compound, m.p. 238°–240° C.

EXAMPLE 10

3,9-DIHYDRO-2-METHYLENE-9-PHENYL-FURO(2,3-b)-1,8-NAPHTHYRIDIN-4(2H)-ONE

A solution of 2 g. of 3,9-dihydro-2-(iodomethyl)-9-phenyl-furo(2,3-b)-1,8-naphthyridin-4(2H)-one in 4 g. of dry piperidine is stirred at room temperature for 72 hours. The reaction mixture is diluted with 80 ml. of water, filtered and the solids washed well with water. The aqueous filtrate is made strongly basic with sodium hydroxide solution and filtered. The combined solids are purified on a grade 62 silica gel column using 5 pts MeOH, 95 pts ethyl acetate as solvent. Fraction III is triturated with 2×50 ml. of hot isopropyl ether yielding the title compound, m.p. 259°–261° C.

EXAMPLE 11

3,9-DIHYDRO-9-PHENYL-2-(1-PYRROLIDINYL-METHYL)-FURO(2,3-b)-1,8-NAPHTHYRIDIN-4(2H)-ONE HYDROCHLORIDE

A mixture of 10.0 g. of 2-(bromomethyl)-3,9-dihydro-9-phenyl-furo(2,3-b)-1,8-naphthyridin-4(2H)-one and 22 g. of pyrrolidine is stirred at room temperature for three hours. The reaction mixture is diluted with 180 ml. of water, the solids washed well with water and air dried. The crude product is treated with excess 1N hydrochloric acid solution, extracted with methylene chloride and the aqueous acidic layer separated. The acidic layer is basified with dilute sodium hydroxide solution, cooled and filtered to yield a crude product, m.p. 159°–160°. Recrystallization from ethyl acetate yields the title compound, m.p. 161°–163°; hydrochloride salt as a hydrate, m.p. 187°–190° C. from ethanol:ether.

EXAMPLE 12

3,5-DIHYDRO-5-(3-CHLOROPHENYL)-2-(HYDROXYMETHYL)-FURO(3,2-c)-1,8-NAPHTHYRIDIN-4(2H)-ONE

In a manner similar to that described in Example 2, treat 2-(bromomethyl)-9-(3-chlorophenyl)-3,9-dihydrofuro(2,3-b)-1,8-naphthyridin-4(2H)-one to yield the title compound, m.p. 243°–245° C.

I claim:

1. A compound represented by the formulae

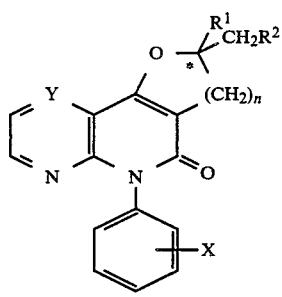 I

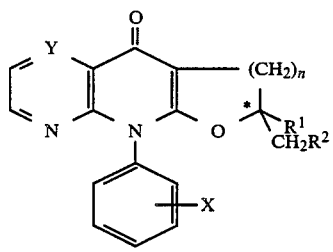 II

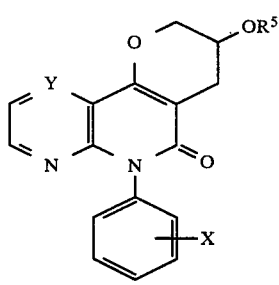 III wherein n is 1 or 2;

$R^1$ and $R^2$ may combined to form a bond, or $R^1$ is hydrogen and $R^2$ is OR, halogen or $NR^3R^4$;

R is hydrogen,

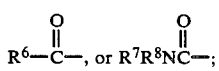

$R^3$ and $R^4$ are independently hydrogen or alkyl having from 1 to 6 carbon atoms, or $R^3$ and $R^4$ may be combined with the nitrogen to which they are attached to form a pyrrolidino, piperidino, morpholino or piperazino ring;

$R^5$ is hydrogen or

$R^6$ is alkyl having from 1 to 9 carbon atoms, alkenyl having from 2 to 7 carbon atoms, alkynyl having from 2 to 7 carbon atoms, phenyl, substituted phenyl wherein the substituents are as defined for X, or benzyl;

$R^7$ and $R^8$ are independently hydrogen, lower alkyl having from 1 to 6 carbon atoms, or hydroxyalkyl having from 1 to 6 carbon atoms;

X is hydrogen, hydroxy, alkyl having from 1 to 6 carbon atoms, alkoxy having from 1 to 6 carbon atoms, nitro, halogen, alkyl-$S(O)_m$ having from 1 to 6 carbon atoms, and wherein m is zero, 1 or 2, or trifluoromethyl; and Y is CH or N; and the acid addition salts thereof.

2. A compound of claim 1 represented by formula I.
3. A compound of claim 1 wherein Y is CH.
4. A compound of claim 1 represented by formula I wherein Y is CH.
5. A compound of claim 4 wherein n is 1.
6. A compound of claim 4 wherein $R^1$ and $R^2$ combine to form a bond.
7. A compound of claim 4 wherein $R^1$ is hydrogen.
8. A compound of claim 7 wherein $R^2$ is OR.
9. A compound of claim 8 wherein R is hydrogen.
10. A compound of claim 8 wherein R is

11. A compound of claim 8 wherein R is

12. A compound of claim 7 wherein $R^2$ is halogen.
13. A compound of claim 7 wherein $R^2$ is $NR^3R^4$.
14. The compound of claim 4 which is 3,5-dihydro-2-(hydroxymethyl)-5-phenyl-furo[3,2-c]-1,8-naphthyridin-4(2H)-one.
15. The compound of claim 4 which is 2-(acetyloxymethyl)-3,5-dihydro-5-phenyl-furo[3,2-c]-1,8-naphthyridin-4(2H)-one.
16. An anti-allergic pharmaceutical composition which comprises an anti-allergic effective amount of a compound having a structural formula as defined in claim 1, in combination with a pharmaceutically acceptable carrier.
17. A method for treating allergic reactions in a mammal which comprises administering an anti-allergic effective amount of the pharmaceutical composition defined in claim 16 to said mammal.
18. A method for treating inflammation in a mammal which comprises administering an anti-inflammatory pharmaceutical composition which comprises an anti-inflammatory effective amount of a compound having a structural formula as defined in claim 1, in combination with a pharmaceutically acceptable carrier to said mammal.

* * * * *